United States Patent
Joshi et al.

(10) Patent No.: US 10,342,753 B2
(45) Date of Patent: Jul. 9, 2019

(54) SKIN CARE COMPOSITIONS CONTAINING LIGHT DIFFUSER POLYMERIC BEADS

(71) Applicant: ROHM AND HAAS COMPANY, Philadelphia, PA (US)

(72) Inventors: Kinjalbahen Joshi, Collegeville, PA (US); Edward La Fleur, Holland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 15/692,108

(22) Filed: Aug. 31, 2017

(65) Prior Publication Data

US 2017/0360685 A1   Dec. 21, 2017

Related U.S. Application Data

(62) Division of application No. 15/102,016, filed as application No. PCT/US2014/069291 on Dec. 9, 2014, now abandoned.

(60) Provisional application No. 61/913,587, filed on Dec. 9, 2013.

(51) Int. Cl.
| | |
|---|---|
| *A61K 8/02* | (2006.01) |
| *A61K 8/81* | (2006.01) |
| *A61Q 1/12* | (2006.01) |
| *A61Q 19/00* | (2006.01) |
| *A61Q 19/08* | (2006.01) |

(52) U.S. Cl.
CPC .......... *A61K 8/8152* (2013.01); *A61K 8/0241* (2013.01); *A61K 8/0266* (2013.01); *A61Q 1/12* (2013.01); *A61Q 19/00* (2013.01); *A61Q 19/007* (2013.01); *A61Q 19/08* (2013.01); *A61K 2800/26* (2013.01)

(58) Field of Classification Search
CPC .............. A61K 8/8152; A61K 2800/26; A61K 8/0241; A61K 8/0266; A61Q 1/12; A61Q 19/00; A61Q 19/007; A61Q 19/08
See application file for complete search history.

(56) References Cited

U.S. PATENT DOCUMENTS

| | | |
|---|---|---|
| 7,776,350 B2 | 8/2010 | Polonka et al. |
| 2001/0038829 A1 | 11/2001 | Hasebe |
| 2001/0053803 A1 | 12/2001 | Kuwahara |
| 2005/0031558 A1 | 2/2005 | Elder et al. |
| 2005/0100568 A1 | 5/2005 | De Mul |
| 2007/0218291 A1* | 9/2007 | Chiou ............... C09D 7/69 428/411.1 |
| 2009/0097123 A1 | 4/2009 | Lafleur |
| 2009/0117162 A1 | 5/2009 | Victor |
| 2010/0266649 A1 | 10/2010 | Maitra |
| 2011/0159060 A1* | 6/2011 | Khan ............... A61K 8/0287 424/401 |
| 2012/0070656 A1 | 3/2012 | Chung et al. |

FOREIGN PATENT DOCUMENTS

| | | |
|---|---|---|
| EP | 1944342 | 7/2008 |
| WO | 20130026657 | 2/2013 |
| WO | 20130095993 | 6/2013 |
| WO | 20130107581 | 7/2013 |

OTHER PUBLICATIONS

International Preliminary Report on Patentability regarding International Application No. PCT/US2014/069291, dated Jun. 14, 2016.
International Search Report and Written Opinion of the International Searching Authority regarding International Application No. PCT/US2014/069291, dated Mar. 10, 2016.

* cited by examiner

*Primary Examiner* — Mark V Stevens
(74) *Attorney, Agent, or Firm* — McDonnell Boehnen Hulbert & Berghoff

(57) ABSTRACT

Disclosed are skin care compositions containing refractive polymeric particles. The composition improves the appearance of skin but reducing gloss without a noticeable presence on the skin surface.

13 Claims, No Drawings

SKIN CARE COMPOSITIONS CONTAINING LIGHT DIFFUSER POLYMERIC BEADS

CROSS-REFERENCE TO RELATED APPLICATIONS

This application is a divisional of U.S. application Ser. No. 15/102,016, filed Jun. 6, 2016, which is a U.S. national phase of International Application No. PCT/US2014/069291, filed Dec. 9, 2014, which claims priority to U.S. Provisional Application No. 61/913,587, filed Dec. 9, 2013, the disclosure of each of which is hereby incorporated by reference in its entirety.

BACKGROUND OF THE INVENTION

Field of the Invention

The invention relates to skin care compositions.

Description of Related Art

Compositions for improving the appearance of skin typically employ an inorganic material in a lotion or powder, where the inorganic material has optical properties capable of changing how light interacts with the skin surface. Typical inorganic materials include, talc, silica, kaolin, or a metal oxide such as zinc, titanium or iron. But these materials can have an undesirable appearance or feel on the skin. There is a need for a skin lotion that is capable of limiting gloss while improving the appearance of skin.

SUMMARY OF THE INVENTION

The disclosed invention provides compositions for use in a skin care. The composition incorporates refractive polymeric particles in a delivery vehicle, such as a lotion, cream, ointment liquid, semi-solid, gel or powder.

In one aspect, the invention provides a composition having:
 a delivery vehicle; and
 polymeric beads, wherein
 the refractive index of the polymer at or near the center of each individual polymeric bead is different than the refractive index of the polymer near the surface of the bead.

The invention also provides a method for making a skin care composition, e.g., a lotion, the method including:
 forming a heated mixture comprising a humectant and an alcohol;
 cooling the combined mixture to about 20° C. to about 40° C.;
 combining the mixture with polymeric beads.

In certain aspects of the invention, the polymeric beads used in the method are those described herein.

These and other features and advantages of the present invention will be more fully understood from the following detailed description of the invention taken together with the claims. It is noted that the scope of the claims is defined by the recitations therein and not by the specific discussion of features and advantages set forth in the present description.

DETAILED DESCRIPTION OF THE INVENTION

The term "polymer" as used herein, is synonymous with "copolymer", "heteropolymer" and "alternating copolymer" and means a large molecule (macromolecule) composed of a repeating series of one or more alternating monomeric species. These sub-units are typically connected by covalent chemical bonds.

The term "alkyl" as used herein, means a straight or branched chain hydrocarbon containing from 1 to 10 carbon atoms unless otherwise specified. The term alkyl includes both saturated and unsaturated hydrocarbons of from 1 to 10 carbon atoms. Saturated alkyl refers to hydrocarbon groups of, for example, 1-10 carbon atoms, and having no sites of unsaturation. Unsaturated alkyl refers to hydrocarbon groups of, for example, 1-10 carbon atoms, and having one or more sites of unsaturation, and includes both alkenyl and alkynyl groups. Alkyl groups may be optionally substituted as described herein.

The term "(meth)acrylate" refers to acrylate, methacrylate, or mixtures thereof.

The term "vinyl benzene monomer" refers to a monomer used in polymerization that includes a benzene ring substituted with one or more vinyl groups. Examples include, but are not limited to styrene and divinyl benzene.

The term "optical contrast" refers to the difference in luminance, reflectance, and/or color that makes an object or surface distinguishable from its surroundings.

As used herein, an "optical contrast effect" refers to the contrast provided when a composition is applied to the skin as compared to the bare skin before the composition was applied.

As used herein, the "center" of a spherical bead refers to a point that is equidistant from all points on the surface of the spherical bead.

The term "near the center" refers to the locations immediately adjacent to the center of a spherical bead.

The term "near the surface" refers to locations in a bead that are immediately under the surface of the bead.

The invention provides a composition having:
 a delivery vehicle; and
 polymeric beads, wherein
 the refractive index of the polymer at or near the center of each individual polymeric bead is different than the refractive index of the polymer near the surface of the bead.

The polymeric beads can be light diffusing and spherical, substantially spherical, or irregularly shaped. The RI of the polymer material can vary continuously within the bead, and as a result, light rays bend with the change in refractive index. The bending of the light rays results in the elimination of light loss through total internal reflection, and the creation of a well-defined focal point and focal length, unique to the spherical bead geometry. The formation of suitable polymeric beads is disclosed in U.S. Pat. No. 7,768,602, which is incorporated herein by reference in its entirety.

The refractive index of the polymer at any location within the individual polymeric beads can be between about 1.4 and about 1.8.

In some embodiments, the polymeric beads are convergent, in that the refractive index (RI) of the polymer at or near the center of the beads is greater than the RI of the polymer near the surface of the beads. In some embodiments, the polymer composition at or near the center of the convergent beads can have a RI that is equal to or greater than about 1.47. In some embodiments, the RI at or near the center of the convergent beads is equal to or greater than about 1.50, 1.51 or 1.52. In other embodiments, the RI of the polymer composition at or near the center of the bead is between about 1.47 and about 1.80, or about 1.50 and about 1.80. In certain embodiments, the RI at or near the center of the convergent beads is about 1.52 to about 1.80, where in other embodiments it is about 1.52 to about 1.60.

In some embodiments, the polymer composition near the surface of the convergent polymeric beads has a RI of less than about 1.47. In other embodiments, the RI of the polymer composition near the surface of the convergent beads is between about 1.40 to about 1.47, or between about 1.40 and 1.49. In certain embodiments, the polymer composition near the surface of the convergent polymeric beads can have a RI of greater than about 1.47, provided that the polymeric composition at or near the center of the bead has a refractive index of about 1.48 or greater.

In some embodiments, the polymeric beads are divergent, in that the RI of the polymer at or near the center of the beads is less than the RI of the polymer near the surface of the beads. In some embodiments, the polymer composition at or near the center of the divergent beads can have a RI that is equal to or less than about 1.50. In some embodiments, the RI at or near the center of the divergent beads is equal to or less than about 1.49, 1.48 or 1.47. In other embodiments, the RI of the polymer composition at or near the center of the divergent beads is between about 1.40 and about 1.47, or about 1.40 and about 1.48. In certain embodiments, the RI at or near the center of the divergent beads is about 1.45 to about 1.49, where in other embodiments, it is about 1.43 to about 1.47.

In some embodiments, the polymer composition near the surface of the divergent polymeric beads has a RI of greater than about 1.47. In other embodiments, the RI of the polymer composition near the surface of the divergent beads is between about 1.50 to about 1.80, or between about 1.50 and 1.60. In certain embodiments, the polymer composition near the surface of the divergent polymeric beads can have a RI of greater than about 1.45, provided that the polymeric composition at or near the center of the bead has a refractive index of about 1.43 or less.

In some embodiments, the difference in refractive index (ΔRI) between the polymer composition at or near the center of the bead and the polymer composition near the surface of the bead is about 0.01 to about 0.4 refractive index units. In some embodiments, the ΔRI is about 0.01 to about 0.2, or about 0.01 to about 0.1. In other embodiments, the ΔRI is about 0.05 to about 0.15, or about 0.05 to about 0.1. There is a positive correlation between the ΔRI of the bead and the optical contrast effect of the bead. Generally, the greater the ΔRI between the polymer at or near the center of the bead and the polymer near the surface of the bead, the greater the optical contrast effect of the bead. A suitable bead or mixture of beads can provide a high optical contrasting effect through the diffused reflection of light without high surface reflectivity (gloss).

In some embodiments, the polymeric beads include a mixture of one or more polymers comprising units derived from (meth)acrylate and/or vinyl-benzene monomers. In some embodiments, the polymeric beads include a mixture of a polymer and a copolymer, or a mixture of two or more different copolymers. The different copolymers can have a different combination of monomeric units, or can have the same mixture of monomeric units in a different ratio. In some embodiments, the polymeric beads can include a mixture of two or more polymers comprising allyl (meth) acrylate, butyl (meth)acrylate, methyl (meth)acrylate, ethyl (meth)acrylate, styrene and divinyl benzene.

In some embodiments, the polymeric beads can have vinyl-benzene derived units, which include, but are not limited to, units derived from styrene and divinyl benzene. The polymeric beads having vinyl-benzene derived units can also include copolymers having units derived from alkyl or alkenyl (meth)acrylate monomers. These monomers include, but are not limited to, allyl (meth)acrylate, butyl (meth)acrylate, methyl (meth)acrylate and ethyl (meth)acrylate. In some embodiments, the copolymer can have acrylate and methacrylate units. For example, the copolymer can have butyl acrylate (BA) and allyl methacrylate (ALMA) units, or methyl methacrylate (MMA) and ethyl acrylate (EA) units. In other embodiments, the copolymer can be a mixture of a polymer and a copolymer. For example, the bead can include a mixture of polystyrene and a copolymer of butyl acrylate (BA) and divinyl benzene (DVB).

In some embodiments, the polymeric beads comprise a copolymer having units derived from butyl acrylate and allyl methacrylate and/or a copolymer having units derived from methyl methacrylate and ethyl acrylate. In some embodiments, the BA/ALMA copolymer has a weight ratio of about 80:20 to about 99:1 BA/ALMA. In some embodiments, the MMA/EA copolymer has a weight ratio of about 80:20 to about 99:1 MMA/EA. Representative copolymer compositions suitable for use in the invention are shown in Table 1.

TABLE 1

Copolymer compositions.

| Copolymer Composition | Weight Ratio |
| --- | --- |
| BA/ALMA | 80:20 |
| BA/ALMA | 85:15 |
| BA/ALMA | 90:10 |
| BA/ALMA | 91:9 |
| BA/ALMA | 92:8 |
| BA/ALMA | 93:7 |
| BA/ALMA | 94:6 |
| BA/ALMA | 95:5 |
| BA/ALMA | 96:4 |
| BA/ALMA | 97:3 |
| BA/ALMA | 98:2 |
| BA/ALMA | 99:1 |
| MMA/EA | 80:20 |
| MMA/EA | 85:15 |
| MMA/EA | 90:10 |
| MMA/EA | 91:9 |
| MMA/EA | 92:8 |
| MMA/EA | 93:7 |
| MMA/EA | 94:6 |
| MMA/EA | 95:5 |
| MMA/EA | 96:4 |
| MMA/EA | 97:3 |
| MMA/EA | 98:2 |
| MMA/EA | 99:1 |
| BA/DVB | 80:20 |
| BA/DVB | 85:15 |
| BA/DVB | 90:10 |
| BA/DVB | 91:9 |
| BA/DVB | 92:8 |
| BA/DVB | 93:7 |
| BA/DVB | 94:6 |
| BA/DVB | 95:5 |
| BA/DVB | 96:4 |
| BA/DVB | 97:3 |
| BA/DVB | 98:2 |
| BA/DVB | 99:1 |

In some embodiments, the polymeric beads include a mixture of two different copolymers or a mixture of a polymer and a copolymer. The mixture can include any of the polymers or copolymers described herein. Where different copolymers are employed, the weight ratio of copolymers in the mixture can range from about 60:40 to about 95:5. In certain embodiments, the weight ratio is about 70:30 to about 85:15. The weight ratio of the mixture of copolymers, or a mixture of a polymer and a copolymer, can be about 60:40, about 65:35, about 70:30, about 75:25, about 80:20, about 85:15, about 90:10 or about 95:5.

In some embodiments, the mixture includes a BA/ALMA copolymer and a MMA/EA copolymer. The weight ratio of the BA/ALMA copolymer to the MMA/EA copolymer can be about 60:40 to about 95:5. In certain embodiments, the weight ratio is 70:30 to 85:15. In certain embodiments, the polymeric beads comprise a copolymer having units of about 92:8 BA/ALMA by weight, and a copolymer having units of about 96:4 MMA/EA by weight. In other embodiments, the polymeric beads comprise a copolymer having units of about 96:4 BA/ALMA by weight, and a copolymer having units of about 96:4 MMA/EA by weight. In some instances, the weight ratio of the BA/ALMA copolymer to the MMA/EA copolymer in the beads is about 80:20.

In certain embodiments, the polymeric beads include about an 80:20 weight ratio of a copolymer of about 92:8 BA/ALMA by weight, and a copolymer of about 96:4 MMA/EA by weight. In a preferred embodiment, these polymeric beads also have a particle diameter of about 0.85 microns.

In other embodiments, the polymeric beads include about an 80:20 weight ratio of a copolymer of about 96:4 BA/ALMA by weight and a copolymer of about 96:4 MMA/EA by weight. In a preferred embodiment, these polymeric beads also have a particle diameter of about 5 microns.

In some embodiments, the polymeric beads comprise a mixture of units derived from butyl acrylate (BA), styrene and divinyl benzene (DVB). In some instances the beads can include polystyrene and a copolymer with a weight ratio of about 80:20 to about 99:1 BA/DVB. The weight ratio of polystyrene to the copolymer can be about 60:40, about 65:35, about 70:30, about 75:25, about 80:20, about 85:15, about 90:10 or about 95:5.

In some embodiments, the beads include polystyrene and a copolymer of BA/DVB. The weight ratio of BA/DVB can be selected from Table 1. In certain embodiments, the beads include polystyrene and a 96:4 copolymer of BA/DVB by weight. The weight ratio of polystyrene to BA/DVB copolymer in the beads can be about 60:40, about 65:35, about 70:30, about 75:25, about 80:20, about 85:15, about 90:10 or about 95:5. In certain embodiments, the weight ratio of the polystyrene to the BA/DVB copolymer in the beads is about 80:20.

In some embodiments, the polymeric beads include about a 80:20 weight ratio of polystyrene and a copolymer of about 96:4 BA/DVB by weight. In a preferred embodiment, these polymeric beads also have a particle diameter of about 2 microns.

In some embodiments, the about 90% or more of the polymeric beads have a particle diameter of about 0.5 micron to about 15 micron. The some instances, the particle diameter is about 0.5 micron to about 1.0 micron, about 1.5 micron to about 2.5 micron, about 4 micron to about 6 micron, about 6 micron to about 10 micron or about 10 micron to about 15 micron. In certain embodiments, the particle diameter is about 0.75 micron to about 0.95 micron, about 1.8 micron to about 2.2 micron, or about 4.8 micron to about 5.2 micron. In some embodiments, about 90% of the polymeric beads have a particle diameter of about 0.5 micron to about 6 micron. In certain embodiments, the about 90% or more of the polymeric beads have a particle diameter of about 0.85 micron. In other embodiments, about 90% or more of the polymeric beads have a particle diameter of about 2 micron. In certain embodiments, about 90% or more of the polymeric beads have a particle diameter of about 5 micron.

In some embodiments, the polymeric beads include a mixture of two or more different types of polymeric beads, where at least one of the polymeric beads is as described herein. The mixture can include one or more polymeric beads described herein, and one or more polymeric beads having the same or substantially the same RI at any location in each individual polymeric bead. In some embodiments, the mixture can include two or more types of polymeric beads described herein, where the bead types have of a different composition and/or particle diameter.

In some embodiments, the mixture can include a first polymeric bead and a second polymeric bead, where the first and second polymeric beads are as described herein. The first and second polymeric beads can have one or more different properties. For example, the first and second polymeric beads can have beads of different particle diameter. In some instances, the portions have beads with different compositions, while in other instances, the portions can have beads that have the same types of polymer subunits, but in different weight ratios. The weight ratio of the first polymeric bead to the second polymeric bead in the mixture can be from about 40:60 to about 90:10. In some embodiments, the weight ratio is about 60:40, about 70:30, or about 90:10. In other embodiments, the weight ratio is about 50:50 or about 80:20.

The first and second polymeric beads can include one or more copolymers having units derived from alkyl or alkenyl (meth)acrylate monomers. In some embodiments, the copolymer can have acrylate and methacrylate units. For example, the first or second polymeric bead can have a copolymer of butyl acrylate (BA) and allyl methacrylate (ALMA) units, and a copolymer of methyl methacrylate (MMA) and ethyl acrylate (EA) units. In other embodiments, the copolymer can be a mixture of a polymer and a copolymer. For example, the bead can include a mixture of polystyrene and a copolymer of butyl acrylate (BA) and divinyl benzene (DVB).

In certain embodiments, the first polymer bead includes about an 80:20 weight ratio of polystyrene and a copolymer of about 96:4 butyl acrylate to divinyl benzene by weight, and the second polymer bead includes about an 80:20 weight ratio of a copolymer of about 96:4 butyl acrylate to allyl methacrylate by weight, and a copolymer of about 96:4 methyl methacrylate to ethyl acrylate by weight. In some embodiments, the weight ratio of first polymeric bead to the second polymeric bead is about 50:50, while in other instances the weight ratio is about 80:20.

In some embodiments, the polymeric beads include a first polymeric bead and a second polymeric bead, where about 90% or more of the first and second beads have a particle diameter as described herein. In some instances, the first and second beads have a different particle diameter. In some embodiments, about 90% or more of the first polymeric bead has a particle diameter of about 0.5 micron to about 3 micron, and about 90% or more of the second polymeric bead has a particle diameter of about 4 micron to about 15 micron. In other embodiments, about 90% or more of the first polymeric bead has a particle diameter of about 1.8 micron to about 2.2 micron, and about 90% or more of the second polymeric bead has a particle diameter of about 4.8 micron to about 5.2 micron. In certain embodiments, about 90% or more of the first polymeric bead has a particle diameter of about 2 micron, and about 90% or more of the second polymeric bead has a particle diameter of about 5 micron.

In some embodiments, the composition can further include one or more inorganic materials. The inorganic material can be a natural or synthetic inorganic pigment. Many inorganic pigments are known in the art, such as, for example, those listed in the Code of Federal Regulations 21, Part 73. In some instances, the inorganic material can be one or more metal oxides. The metal-oxide can include, but is not limited to, $TiO_2$, $Fe_2O_3$, $CaCO_3$, SnO, $SnO_2$, $MgSiO_3$, $Cr_2O_3$, ZnO, MgO, ZnS, $ZrO_2$, CuO, $MgF_2$, $Ce_2O_3$, $CeO_2$, $Y_2O_3$, $CaF_2$, $Al_2O_3$, $BaSO_4$, BiOCl, $SiO_2$, glass flake mica, talc, kaolin and mixtures thereof. In some embodiments, the inorganic materials include iron oxide. Non-limiting examples of metal-oxide pigments include pigments marketed under the trade designations Xirana®, Colorona®, Timiron®, Dichrona®, Microna®, Soloron®, Prestige®, Flonac®, Flamenco®, Timica®, Duochrome®, and mixtures thereof.

The concentration of the inorganic materials (e.g., iron oxide) can range from about 0.01 to about 5% by weight of the composition. In certain instances, the concentration of the inorganic materials ranges from about 0.1 to about 2 weight % of the composition.

Depending on the delivery vehicle, the composition can be in the form of a lotion, cream, ointment, liquid, semisolid, gel or powder. The delivery vehicles can differ by the presence and/or amount of their components, which can include, but do not require nor are limited to, humectants, thickening agents, fatty alcohols, emulsifiers, waxes, additives, oils, inorganic compounds, clays, fillers, binders and water. In some embodiments, the delivery vehicle (and therefore the composition) is water-based, while in other embodiments, the delivery vehicle is oil-based. In certain instances, the delivery vehicle is an emulsion of oil and water, while in other embodiments the delivery vehicle is substantially free of water.

In some embodiments, the composition is a lotion, where the delivery vehicle is a lotion base. The lotion base includes lotions, crèmes, ointments and moisturizers known in the art. A suitable lotion base includes, for example, a humectant, a thickening agent, a fatty alcohol, an emulsifier, a wax, an additive and water. In some embodiments, the lotion base is water-based, while in other embodiments, the lotion base is oil-based. In certain instances, the lotion base is an emulsion of oil and water.

In some embodiments, the composition is a powder where the delivery vehicle is a powder base. A powder base is a solid at room temperature (La, between about 15° C. to 25° C.), although the powder base may be liquid above and/or below room temperature. A suitable powder base includes, for example, inorganic compounds (i.e., silica, talc, metal oxide), clays, fillers and binders, and be substantially free of water.

In some embodiments, the composition is a liquid, where the delivery vehicle is a liquid base. A liquid base is a liquid at room temperature (i.e., between about 15° C. to 25° C.), although the liquid base may be liquid above and/or below room temperature. A liquid base should be sufficiently free flowing to be filled into containers by pouring, but should be of sufficient viscosity to remain on the skin without running. A suitable liquid base includes, for example, a wax and/or an oil, and typically has a greater amount of water by weight than the lotion base, semi-solid base and powder base.

In some embodiments, the composition is a semi-solid or gel, where the delivery vehicle is a semi-solid or gel base, respectively. The semi-solid or gel base has the consistency of a paste or gel at room temperature (i.e., between about 15° C. to 25° C.), although the semi-solid and gel bases may be a paste or gel above and/or below room temperature. A suitable semi-solid or gel base typically has a greater amount of water by weight than the powder base, but a lesser amount of water by weight than the lotion base and the liquid base.

The humectant can be chosen from diols, diol analogs, triols, triol analogs, polymeric polyols, or mixtures thereof. Numerous humectants are known in the art. A non-limiting list of example humectants includes glycols, such as propylene glycol, hexylene glycol and butylene glycol, glyceryl triacetate, vinyl alcohol, neoagarobiose, sugar polyols such as glycerol, sorbitol, xylitol and maltitol, polymeric polyols such as, polydextrose, urea, glycerin, aloe vera gel, 2-methyl-1,3-propandiol (mp diol), alpha hydroxy acids such as lactic acid, and honey. In certain examples, the humectant can be glycerin or polysorbate The humectant can also be a surfactant. The surfactant can be nonionic, anion, cationic or zwitterionic. A non-limiting list of example surfactants includes monoglycerides, lecithins, glycolipids, fatty alcohols, fatty acids, polysaccharides, sorbitan esters and polysorbates (polysorbate 20, 40, 60, 65 and 80, for example). In certain embodiments, the humectant can be a polysorbate, such as polysorbate 20 or polysorbate 80, or a mixture including one or more polysorbates.

In some embodiments, the humectant can include a combination of one or more humectants. For example, in some instances the humectant can be a mixture of a polyol and a surfactant, such as polysorbate 20 and glycerin.

The humectant can be present in the composition in an amount ranging from about 2% to about 15% by weight. The amount can be varied to obtain the desired properties of the resulting composition, such as stability in slightly aqueous environments, dissolution in highly aqueous environments, and the ability to incorporate a payload and optional additives. In some embodiments, the humectant is present as about 0.5% to about 10%, or about 1% to about 5% of the composition by weight. In certain embodiments, the humectant can be about 2% of the composition by weight.

The thickening agent is a substance added to the delivery vehicle to increase viscosity. The thickening agent can also increase the stability of the delivery vehicle by improving the suspension of other components in the delivery vehicle. Thickening agents include viscous liquids, rheology modifiers, synthetic polymers and vegetable gums. For example, the thickening agent can be polyethylene glycol, polyacrylic acid, acrylates or polysaccharides such as xanthan gum, agar, alginic acid, sodium alginate, carrageenan, gum arabic, gum ghatti, gum tragacanth, karaya gum, guar gum, locust bean gum, beta-glucan, chicle gum, dammar gum, glucomannan, mastic gum, spruce gum or tara gum. In some embodiments, the delivery vehicle includes a thickening agent that is about 0.5 to about 1.4% of the composition by weight. In certain embodiments, the thickening agent is present in about 0.7% of the composition by weight.

The fatty alcohol is an organic compound having a long, aliphatic carbon chain and a primary alcohol group. The aliphatic chain is typically a straight chain with no branching, and can have four to 26 carbon atoms. In some instances the fatty alcohol is branched or has unsaturation. Fatty alcohols include, but are not limited to butenyl alcohol, cetearyl alcohol, cetyl alcohol, isocetyl alcohol, isostearyl alcohol, lauryl alcohol, myristyl alcohol, stearyl alcohol, lanolin alcohol. In some embodiments, the delivery vehicle includes a fatty alcohol in about 1.0 to about 5.0% of the composition by weight.

The emulsifier is a substance that stabilizes a mixture of immiscible components in a miscible state, i.e. stabilizes an emulsion. The emulsifier can also be a surfactant. The emulsifier can include, but is not limited to, stearates, polysorbates, lecithin and mixtures therefore. Stearates include vegetable based stearic acid, such as palm stearic, sorbitan monostearate, sorbitan distearate, sorbitan tristearate, glyceryl monostearate, glyceryl distearate, sodium stearate, calcium stearate, magnesium stearate, and mixtures thereof. Polysorbates include polysorbate 20, polysorbate 40, polysorbate 60, polysorbate 80 and mixtures thereof. In some embodiments, the delivery vehicle includes an emulsifier in about 1.0 to about 5.0% of the composition by weight. In certain embodiments, the emulsifier is present in about 2% of the composition by weight.

The wax can include a water insoluble chemical compound, or mixture of compounds that are malleable solids at ambient temperature. The wax can be synthetic or naturally occurring, such as animal waxes, vegetable waxes, mineral waxes and petroleum waxes. The animal wax can include beeswax, Chinese wax, earwax, lanolin, shellac or spermaceti. The mineral wax can include ceresin wax, montan wax, ozocerite or peat waxes. Petroleum waxes can be paraffin wax, microcrystalline wax and petrolatum. In some embodiments, the delivery vehicle includes a wax in about 1.0% to about 10.0% of the composition by weight. In certain embodiments, the wax is present in about 5% of the composition by weight.

In some embodiments, the delivery vehicle further includes one or more additives. The additive can be any component added to obtain a desired property of the resulting composition. Additives can include coloring agents, preservatives, antibiotics, herbs, botanicals, vitamins, sunscreen agents and pharmaceutical agents. In some embodiments, the composition includes an additive in about 0.001 to about 10.0% by weight. In certain embodiments, the additive is present in about 1% to about 5% of the composition by weight.

Coloring agents are used in amounts effective to produce the desired color and include natural food colors and dyes suitable for food, drug and cosmetic applications (FD&C dyes). The coloring agents may be water-soluble, and include, in a non-limiting listing, Blue No. 1 (ethyl-[4-[[4-[ethyl-[(3-sulfophenyl)methyl]amino]phenyl]-(2-sulfophenyl)methylidene]-1-cyclohexa-2,5-dienylidene]-[(3-sulfophenyl)methyl]azanium), FD&C Blue No. 2 (disodium salt of 5,5-indigotindisulfonic acid), Green No. 3 (ethyl-[4-[[4-[ethyl-[(3-sulfophenyl)methyl]amino]phenyl]-(4-hydroxy-2-sulfophenyl)methyl idene]-1-cyclohexa-2,5-dienylidene]-[(3-sulfophenyl)methyl] azanium), Red No. 40 (disodium 6-hydroxy-5-((2-methoxy-5-methyl-4-sulfophenyl)azo)-2-naphthalenesulfonate) Red No. 3 (2-(6-Hydroxy-2,4,5,7-tetraiodo-3-oxo-xanthen-9-yl)benzoic acid) Yellow No. 5 (trisodium 1-(4-sulfonatophenyl)-4-(4-sulfonatophenylazo)-5-pyrazolone-3-carboxylate)) and Yellow No. 6 (Disodium 6-hydroxy-5-[(4-sulfophenyl)azo]-2-naphthalenesulfonate). In some embodiments, the coloring agent is titanium dioxide ($TiO_2$). The coloring agent may include a mixture of coloring agents. The amount of coloring agent used in the composition is determined depending on the color desired and the extent of the color desired.

In some embodiments, the additive can be a preservative. The choice of preservative will depend on the desired properties of the preservative. Various preservatives are known in the art, non-limiting examples include sodium benzoate and potassium sorbate. A preservative, or combination thereof, can be added in amounts of about 0.001 wt % to about 5 wt %, preferably of about 0.1 wt % to about 1.5 wt % of the composition by weight.

Anti-microbial agents include compounds that upon release from the composition interact with microbes in the environment, such as an antibacterial or antifungal agent. Examples include antibiotics, such as tricloscan, and antifungals, such as polyenes and azoles (imidazoles, triazoles and thiazoles).

Herbal and botanical agents and include plant roots, stems, roots, tuber, extracts, etc. that have a use, or perceived use, as a health supplement. Other herbs and botanicals have use for a variety of physiological effects, ranging from alertness to anti-hypertension.

Vitamins and pharmaceutical substances can include, but are not limited to resveratrol, retinol, such as retinyl palmitate, epidermal growth factor, alpha hydroxy acids (AHAs), beta hydroxy acids, peptides, such as Matryxil and copper peptides, coenzyme Q10, argireline, anti-oxidants and vitamin C.

Sunscreen agents include compounds that can act as a sunscreen or sunblock by blocking or absorbing ultraviolet light. Sunscreen agents can be organic or inorganic compounds, and can absorb specific ranges of ultraviolet light (e.g., UVA or UVB light), or absorb wider ranges of wavelengths (i.e., broad spectrum sunscreens). Sunscreen agents can include, for example, $TiO_2$, $ZnO_2$, p-aminobenzoic acid (PABA), octyldimethyl-PABA, phenylbenzimidazole sulfonic acid, 2-ethoxyethyl p-methoxycinnamate, dioxybenzone, oxybenzone, homomethyl salicylate, menthyl anthranilate, 2-cyano-3,3-diphenyl acrylic acid, 2-ethylhexyl-paramethoxycinnamate, 2-ethylhexyl salicylate, 2-hydroxy-4-methoxybenzophenone-5-sulfonic acid, 3-benzoyl-4-hydroxy-6-methoxybenzenesulfonic acid, triethanolamine salicylate, 1-(4-methoxyphenyl)-3-(4-tert-butylphenyl)propane-1,3-dione, butyl methoxy dibenzoylmethane, or composition thereof, can be an additive in the composition. In some embodiments, The composition can include a sunscreen agent in about 0.01 to about 10.0% by weight. In certain embodiments, the additive is present in about 1% to about 5% by weight of the composition.

The composition can include about 1% to about 15% polymeric beads by weight. The polymeric beads can be any of the polymeric beads described herein, or a mixture thereof. In some embodiments, the composition can include about 1% to about 5%, or about 5% to about 10%, or about 10% to about 15% polymeric beads by weight. In certain embodiments, the composition can include about 1% to about 2%, about 2% to about 4%, about 4% to about 6%, about 6% to about 8%, or about 9% to about 11% polymeric beads by weight. In certain embodiments, the composition can include about 1.5%, 3%, 5%, 7% or 10% polymeric beads by weight. In other embodiments, the skin care composition can also include about 50% to about 85% water by weight.

The invention also provides a method for making a skin care lotion, the method including:

heating a first mixture comprising a humectant and a thickening agent to about 60° C. to about 100° C.;

heating as second mixture comprising an alcohol and an emulsifier to about 60° C. to about 100° C.;

combining the first and second mixtures and cooling the combined mixture to about 20° C. to about 45° C.;

adding polymeric beads to the combined mixture.

The humectant and a thickening agent in the first mixture of the method can be as described herein. In some embodiments of the method, the first mixture is heated to about 70° C. to about 90° C. In certain embodiments, the first mixture is heated to about 85° C.

The alcohol and emulsifier in the second mixture of the method can be as described herein. In some embodiments of the method, the second mixture is heated to about 70° C. to about 90° C. In certain embodiments, the second mixture is heated to about 85° C.

The polymeric beads of the method can be as described herein. In some embodiments, the polymeric beads are added to the combined mixture when the combined mixture is between about 20° C. and about 40° C. In other embodiments, the temperature is about 30° C. to about 40° C., or about 35° C.

EXAMPLES

Example 1: Preparation of Lotion Base (Control)

| Component | Percent by Weight |
|---|---|
| Deionized water | 86.3 |
| Keltrol CG-SFT (Xanthan Gum) | 0.7 |
| Glycerin | 2 |
| Cetostearyl Alcohol | 3 |
| Glyceryl Monostearate | 2 |
| Petrolatum | 5 |
| Optiphen (preservative) | 1 |

A mixture of Keltrol CG-SFT and glycerin in water was heated to 65° C. and stirred with an overhead mixer. The resulting solution was heated to 85° C. while stirring continued. A separate mixture of cetostearyl alcohol and glyceryl monostearate were heated to 85° C. and mixed until a solution was obtained. The two solutions were combined, and the resulting mixture was mixed as it cooled. When the mixture cooled to 35° C., the preservative was added and the mixture was mixed for 10 minutes. Citric acid and/or water were added as needed.

Example 2: Preparation of Lotion Comprising Polymeric Beads

| Trade Name | Lotion A | Lotion B | Lotion C | Lotion D | Lotion E |
|---|---|---|---|---|---|
| Polymeric beads (wt %) | 1.5% | 3% | 5% | 7% | 10% |
| Deionized water (wt %) | 79.8% | 73.3% | 64.6% | 56% | 43% |
| Keltrol CG-SFT (wt %) (Xanthan Gum) | 0.7% | 0.7% | 0.7% | 0.7% | 0.7% |
| Glycerin (wt %) | 2% | 2% | 2% | 2% | 2% |
| Cetostearyl Alcohol (wt %) | 3% | 3% | 3% | 3% | 3% |
| Glyceryl Monostearate (wt %) | 2% | 2% | 2% | 2% | 2% |
| Petrolatum (wt %) | 5% | 5% | 5% | 5% | 5% |
| Light diffusing Particles (wt %) | 5% | 10% | 16.7% | 23.3% | 33.3% |
| Optiphen (preservative) (wt %) | 1% | 1% | 1% | 1% | 1% |

A mixture of Keltrol CG-SFT and glycerin in water was heated to 65° C. and stirred with an overhead mixer. The resulting solution was heated to 85° C. while stirring continued. A separate mixture of cetostearyl alcohol and glyceryl monostearate were heated to 85° C. and mixed until a solution was obtained. The two solutions were combined, and the resulting mixture was mixed as it cooled. When the mixture cooled to 35° C., the polymeric beads were added and the resulting mixture was mixed at 35° C. for 30 minutes. The preservative was added and the mixture was mixed for 10 minutes. Citric acid and/or water were added as needed.

Lotions were made according to this procedure with polymeric beads having particle diameters of 0.85 µm, 2 µm, 5 µm, and a mixture of 2 µm and 5 µm. The compositions of the beads are listed below:

| Particle Size | Components |
|---|---|
| 0.85 micron | 80% 92:8 copolymer of BA/ALMA<br>20% 96:4 copolymer of MMA/EA |
| 2 micron | 90% polystyrene<br>10% 96:4 copolymer of BA/DVB |
| 5 micron | 80% 96:4 copolymer of BA/ALMA<br>20% 96:4 copolymer of MMA/EA |

The compositions of the lotions are listed below:

| Lotion | Polymeric Bead Diameter | Weight Percent of Polymeric Beads |
|---|---|---|
| 1A | 0.85 µm | 1.5 |
| 1B | 0.85 µm | 3 |
| 1C | 0.85 µm | 5 |
| 1D | 0.85 µm | 7 |
| 1E | 0.85 µm | 10 |
| 2A | 2 µm | 1.5 |
| 2B | 2 µm | 3 |
| 2C | 2 µm | 5 |
| 2D | 2 µm | 7 |
| 2E | 2 µm | 10 |
| 3A | 5 µm | 1.5 |
| 3B | 5 µm | 3 |
| 3C | 5 µm | 5 |
| 3D | 5 µm | 7 |
| 3E | 5 µm | 10 |
| 4A | 80:20 2 µm/5 µm | 1.5 |
| 4B | 80:20 2 µm/5 µm | 3 |
| 4C | 80:20 2 µm/5 µm | 5 |
| 4D | 80:20 2 µm/5 µm | 7 |
| 4E | 80:20 2 µm/5 µm | 10 |
| 5A | 50:50 2 µm/5 µm | 1.5 |
| 5B | 50:50 2 µm/5 µm | 3 |
| 5C | 50:50 2 µm/5 µm | 5 |
| 5D | 50:50 2 µm/5 µm | 7 |
| 5E | 50:50 2 µm/5 µm | 10 |

Example 3: Determination of Visual Soft Effect

The inventive compositions were compared with commercially available compositions of inorganic iron oxide (Control Sample #1), gold mica (pearlizing agent) (Control Sample #2), and the base lotion (Control Sample #3). Lotions 1A-3E were applied to synthetic skin with N19 topography and the visual appearance on the synthetic skin surface was evaluated according to the following procedure:
Cut 1.5×1.5 inch skin piece;
Apply 0.1 ml of lotion on top of skin surface;
Rub with finger about 1 minute;
Dry for one hour before quantifying, by imaging, the appearance.

Visual evaluation: compared to Control Samples #1-3, Lotions 1A-3E exhibited superior mattifying (gloss reducing) properties on the synthetic skin surface.

Example 4: Gloss Measurement

The mattifying properties of the lotion can be determined by measuring the gloss of the lotion with a spectrophotometer. The samples in Example 3 were analyzed with a BYK Gardner Spectro-guide 45/0 gloss meter. Values are recorded in gloss units (GU) at a viewing angle of 60°:

|  | Control #1 (iron oxide) | Control #2 (gold mica) | Control #3 (base lotion) | | |
|---|---|---|---|---|---|
| Gloss | 2.7 | 3.9 | 5.8 | | |
| Particle | Beads Percentage by Weight | | | | |
| Size | 1.5% (A) | 3% (B) | 5% (C) | 7% (D) | 10% (E) |
| 0.85 μm (1) | 5.9 | 4.6 | 5.3 | 3.5 | 3.5 |
| 2 μm (2) | 4.8 | 4.2 | 4.8 | 4.4 | 4.8 |
| 5 μm (3) | 4.4 | 4.7 | 3.8 | 4.3 | 3.6 |

What is claimed is:

1. A method for improving the appearance of skin while limiting gloss on the skin, the method comprising applying to the skin a composition comprising a mixture of polymeric beads, wherein the mixture of polymeric beads consists of first polymeric beads and second polymeric beads, wherein the first and second polymeric beads have different compositions, and each of the first polymeric beads consists of a mixture of a first polymer and a second polymer, wherein the first polymer is polystyrene and the second polymer is a copolymer consisting of first monomeric units and second monomeric units at a weight ratio of first monomeric units to second monomeric units of from about 80:20 to about 99:1; wherein the first and second monomeric units are different and selected from allyl (meth)acrylate, butyl (meth)acrylate, methyl (meth)acrylate, ethyl (meth)acrylate, and divinyl benzene.

2. The method of claim 1, wherein the composition comprises a delivery vehicle which is a lotion, cream or ointment base.

3. The method of claim 1, wherein the composition comprises a delivery vehicle which is a powder base.

4. The method of claim 1, wherein about 90% or more of the first polymeric beads have a particle diameter of about 1.8 micron to about 2.2 micron; and about 90% or more of the second polymeric beads have a particle diameter of about 4.8 micron to about 5.2 micron.

5. A method for improving the appearance of skin while limiting gloss on the skin, the method comprising applying to the skin a composition comprising a mixture of polymeric beads, wherein the mixture of polymeric beads consists of first polymeric beads and second polymeric beads, wherein the first polymeric bead consists of polystyrene and a copolymer of butyl acrylate and divinyl benzene, wherein the weight ratio of butyl acrylate to divinyl benzene in the copolymer is from 90:10-96:4; and the second polymeric bead comprises a copolymer of methyl methacrylate and ethyl acrylate at a weight ratio of methyl methacrylate to ethyl acrylate of 90:10-96:4.

6. A method according to claim 5, wherein the weight ratio of the first polymeric beads to the second polymeric bead is about 60:40 to about 95:5.

7. A method for improving the appearance of skin while limiting gloss on the skin, the method comprising applying to the skin a composition comprising a mixture of polymeric beads, wherein the mixture of polymeric beads consists of first polymeric beads and second polymeric beads, wherein the first polymeric beads consist of a mixture of polystyrene and a copolymer of butyl acrylate and divinyl benzene; and the second polymeric beads consist of a mixture of a copolymer of butyl acrylate and allyl methacrylate, and a copolymer of methyl methacrylate and ethyl acrylate.

8. The method of claim 5, wherein the composition comprises a delivery vehicle which is a lotion, cream or ointment base.

9. The method of claim 5, wherein the composition comprises a delivery vehicle which is a powder base.

10. The method of claim 5, wherein about 90% or more of the first polymeric beads have a particle diameter of about 1.8 micron to about 2.2 micron; and about 90% or more of the second polymeric beads have a particle diameter of about 4.8 micron to about 5.2 micron.

11. The method of claim 7, wherein the composition comprises a delivery vehicle which is a lotion, cream or ointment base.

12. The method of claim 7, wherein the composition comprises a delivery vehicle which is a powder base.

13. The method of claim 7, wherein about 90% or more of the first polymeric beads have a particle diameter of about 1.8 micron to about 2.2 micron; and about 90% or more of the second polymeric beads have a particle diameter of about 4.8 micron to about 5.2 micron.

* * * * *